(12) United States Patent
Börner et al.

(10) Patent No.: US 6,417,385 B1
(45) Date of Patent: Jul. 9, 2002

(54) METHOD OF PRODUCING ACETONE-CYANHYDRIN

(75) Inventors: Walter Börner, Freigericht; Liane Deusser, Erzhausen; Ralph Marquardt, Frankfurt am Main, all of (DE); Rudolf Vanheertum, Brasschaat (BE); Karl-Heinz Vieweg, Freigericht (DE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 09/959,271

(22) PCT Filed: Mar. 8, 2000

(86) PCT No.: PCT/EP00/02014

§ 371 (c)(1),
(2), (4) Date: Dec. 28, 2001

(87) PCT Pub. No.: WO00/64861

PCT Pub. Date: Nov. 2, 2000

(30) Foreign Application Priority Data

Apr. 22, 1999 (DE) .......................... 199 18 246

(51) Int. Cl.$^7$ .............................. C07C 253/30
(52) U.S. Cl. ....................... 558/346; 558/351
(58) Field of Search .................. 558/346, 351

(56) References Cited

U.S. PATENT DOCUMENTS 3,700,718 A   10/1972   Yamagishi et al.

FOREIGN PATENT DOCUMENTS

DE   1 257 765   1/1968
EP   0 421 237   9/1990

OTHER PUBLICATIONS

Ullmann's Encyclopedia of Industrial Chemistry 5$^{th}$ Edn. (1985), pp. 91–92 [sic].

Ullmann's Encyclopedia of Technical [sic] Chemistry, 5$^{th}$ Edn. (1987), vol. A8, pp. 161–163.

Primary Examiner—Joseph K. McKane
Assistant Examiner—Sonya Wright
(74) Attorney, Agent, or Firm—Smith, Gambrell & Russell, LLP

(57) ABSTRACT

Acetone-cyanhydrin can be produced in a gas-liquid reactor from a hydrogen cyanide-containing gas, especially the crude gas originating from a methane-ammonia (BMA) or Andrussow process, and acetone in the presence of a base. The aim of the invention is to overcome the disadvantages of the methods for producing acetone-cyanhydrin known from the art. To this end, the gaseous phase removed from the reactor is liberated from the unreacted acetone and hydrogen cyanide in a gas purifier that is operated with a high-boiling solvent, especially with stabilized acetone-cyanhydrin, and the washed phase is fed to the gas-liquid reactor.

10 Claims, No Drawings

METHOD OF PRODUCING ACETONE-CYANHYDRIN

This application is a 371 of PCT/EP00/0214 filed Mar. 8, 2000.

DESCRIPTION

The invention is directed towards an improved process for the continuous production of acetone cyanohydrin from hydrogen cyanide and acetone, whereby hydrogen cyanide in the form of a gas mixture containing inert other gases, in particular in the form of a crude gas arising from the BMA process or the Andrussow process, is employed for the purpose of producing hydrogen cyanide.

Acetone cyanohydrin, that is to say α-hydroxyisobutyronitrile, is the most important initial product for all derivatives of methacrylic acid and, above all, the esters thereof. Technically, acetone cyanohydrin is produced by base-catalysed addition of hydrogen cyanide (hydrocyanic acid) onto acetone. In the neutral range and especially in the alkaline range, acetone cyanohydrin is in equilibrium with its initial components. The commercial processes predominantly utilise liquid-phase processes which are carried out both discontinuously and continuously in the presence of catalysts such as caustic soda solution, caustic potash solution, potassium carbonate, sodium acetate/acetic acid, pyridine/acetic acid as well as anion-exchange resins at temperatures below 40° C. Attention is drawn, in exemplary manner, to the process due to Rohm and Haas (see Ullmann's Encyclopedia of Industrial Chemistry $5^{th}$ Edn. (1985), pages 91–92 [sic]): In this process, liquid hydrocyanic acid, acetone and a basic catalyst are introduced continuously into a reactor and subsequently, after stabilisation with sulfuric acid and filtration of the catalyst by a two-stage distillation, the reaction mixture is freed firstly of unconverted hydrocyanic acid and acetone and then of water. The waste gases from the first distillation stage are recycled into the reactor, pure stabilised acetone cyanohydrin is withdrawn at the bottom of the second distillation stage. A disadvantage of this process is the fact that hydrogen cyanide has to be liquefied from a gas containing hydrogen cyanide, for example a crude gas arising from the BMA process or the Andrussow process for the production of hydrogen cyanide. The technical devices for liquefying gaseous hydrocyanic acid and for storing the liquid hydrocyanic acid give rise to high investment costs and high variable costs of liquefaction, inter alia as a result of the use of cooling brines. A further consideration is that a relatively large stock of liquid hydrocyanic acid conflicts with the Responsible Care Programme.

Instead of liquefied hydrocyanic acid, it is also known to employ a gas mixture containing hydrogen cyanide and inert gases, for example coke-oven gases, in a process for producing acetone cyanohydrin. In the process due to Reinpreussen AG—see Ullmann's Encyklopädie der Technischen Chemie, $4^{th}$ Edition, Volume 7, pages 34–35—coke-oven gases containing hydrogen cyanide are washed continuously, after a potash wash, in countercurrent with acetone which contains 10% water, and the reaction to form acetone cyanohydrin is carried out in the presence of a basic catalyst in two gas-washing columns connected in series; the processing of the reaction mixture containing acetone cyanohydrin encompasses two acetone columns and two columns for purifying the acetone cyanohydrin. Despite the very elaborate plant, it is not possible to avoid a large quantity of the acetone and also some of the unconverted hydrogen cyanide being discharged together with the waste gas emerging from the second gas-washing column.

According to DE-AS 12 57 765 it is possible for acetone cyanohydrin to be obtained from gases containing dilute gaseous hydrogen cyanide arising from the synthesis of hydrocyanic acid from methane and ammonia, i.e. from the crude gas of the BMA process, by the gas being introduced into liquid acetone or into a solution of acetone in an inert solvent such as acetone cyanohydrin at a pH value from 8 to 8.5, by the conversion being carried out at 0 to 25° C. and by the pH value of the reaction mixture being constantly maintained by addition of baryta solution. Together with the inert gases discharged from the reactor, a quantity of acetone corresponding to the phase equilibrium as well as unconverted hydrocyanic acid are also inevitably discharged—as shown by the examples in this document, hydrogen cyanide breaks through in a quantity amounting to approximately 0.5 to 7.2%, relative to the quantity of hydrocyanic acid employed. Accordingly, the embodiments described in this document are hardly suitable for carry-over onto a technical scale or they necessitate at least a subsequent processing of the waste gas with a view to recovering acetone and unconverted hydrocyanic acid. A further disadvantage consists in the fact that the pH value is adjusted by means of baryta solution; accordingly, the liquid phase containing acetone cyanohydrin, after the stabilisation thereof with sulfuric acid prior to the purification by distillation, has to be passed across a filter with a view to separating barium sulfate. In the case of the embodiment described in this document, by virtue of the inert gases that are introduced with the gas mixture containing HCN the equilibrium of the formation of acetone cyanohydrin is steadily shifted in the direction of the initial products, so that a discharge of acetone and hydrogen cyanide is unavoidable. Even if acetone and gas containing hydrogen cyanide are supplied continuously to the circulating reactor which is operated in accordance with the air-lift principle and which is filled with acetone cyanohydrin, the discharge of reactants cannot be avoided, because a pH value of 8 to 8.5 is maintained in the reactor.

The object of the present invention is accordingly to demonstrate an improved process for producing acetone cyanohydrin, in which a gas mixture containing hydrogen cyanide and inert gases is employed, in particular a crude gas arising from the BMA process or the Andrussow process. A process for the continuous production of acetone cyanohydrin has been found, comprising conversion of hydrogen cyanide with acetone in the presence of a basic catalyst and acetone cyanohydrin in a gas/liquid reactor to which acetone and a gas mixture containing hydrogen cyanide and inert gases are supplied continuously and from which a liquid phase containing acetone cyanohydrin and a gas phase containing the inert gases are carried away, and separation of volatile constituents from the liquid phase by distillation, said process being characterised in that the gas phase which is carried away out of the reactor is freed of unconverted hydrogen cyanide and acetone in a gas-washer which is subjected to the action of a solvent boiling at 100 to 200° C. (normal pressure) or of stabilised pure acetone cyanohydrin, and the washed phase which is obtained is supplied to the gas/liquid reactor. The dependent claims are directed towards preferred embodiments of the process according to the invention.

By way of wash liquid, use is made of the gas phase emerging from the gas/liquid reactor, which contains the inert gases of the gas mixture containing hydrogen cyanide that is employed as well as acetone and unconverted hydrocyanic acid, with an inert solvent, in particular a solvent forming azeotropes with water and having a boiling-point above 100° C. (normal pressure). This solvent preferably exhibits a boiling-point in the range from 150 to 200° C., but higher or lower boiling-points are also possible, assuming that the solvent can be separated without difficulty from acetone, on the one hand, and from acetone cyanohydrin, on the other hand. The term 'inert' is to be understood to mean that the solvent does not enter into a reaction with hydrogen cyanide, acetone or acetone cyanohydrin under the conditions of operation.

According to an alternative embodiment, stabilised pure acetone cyanohydrin is supplied to the gas-washer by way of wash liquid instead of the stated solvent. A feature essential to the invention is that the stabilised pure acetone cyanohydrin is an acidically stabilised product substantially free of acetone and hydrogen cyanide. In expedient manner, some of the acetone cyanohydrin which is generated in accordance with the invention is recycled into the gas-washer after the stabilisation of said acetone cyanohydrin with an acid, in particular sulfuric acid or phosphoric acid, and after separation of acetone and unconverted hydrocyanic acid by distillation. The liquid phase emerging from the washer subsequently flows through the gas/liquid reactor. The waste gas emerging from the gas-washer is substantially free of hydrogen cyanide and acetone.

The quantity of wash liquid for the gas-washer depends crucially on the throughput of the gas containing hydrogen cyanide, on the solubility of hydrogen cyanide in the wash medium and also on the reaction temperature. With the preferred use of stabilised pure acetone cyanohydrin by way of wash liquid, the gas-washer is expediently subjected to the action of approximately 0.3 to 3 moles of stabilised pure acetone cyanohydrin per mole of the hydrogen cyanide introduced into the reactor. By employing a crude gas containing hydrogen cyanide with an HCN content of approximately 22 to 23 vol. % (=BMA crude gas), a quantitative ratio of 0.5 to 2 moles of acetone cyanohydrin per mole of hydrogen cyanide has proved to be expedient. The higher the rate of feed of hydrogen cyanide, the higher also will be the quantity of wash liquid to be used.

A BMA crude gas or an Andrussow crude gas is preferably employed in the process according to the invention. The gas mixture resulting from the stated conventional processes for producing hydrogen cyanide can be used as such or after an acid washing. The crude gas arising from the BMA process, in which hydrocyanic acid and hydrogen are substantially formed from methane and ammonia, typically contains, according to Ullmanns's Encyclopedia of Technical [sic] Chemistry, 5$^{th}$ Edn. (1987), Vol. A8, pp. 161–163, 22.9 vol. % HCN, 71.8 vol. % $H_2$, 2.5 vol. % $NH_3$, 1.1 vol. % $N_2$ and 1.7 vol. % $CH_4$. In the known Andrussow process, hydrocyanic acid and water are formed from methane, ammonia and atmospheric oxygen. The crude gas of the Andrussow process typically contains, when atmospheric oxygen is employed by way of oxygen source in accordance with the previously cited document, 8 vol. % HCN, 22 vol. % $H_2$, 46.5 vol. % $N_2$, 15 vol. % $H_2O$, 5 vol. % CO, 2.5 vol. % $NH_3$ and, in each case, 0.5 vol. % $CH_4$ and $CO_2$.

In the case where a crude gas arising from the BMA process or the Andrussow process is employed that has not been subjected to acid washing, the ammonia contained in the crude gas acts as a catalyst for the process according to the invention. The ammonia contained in the crude gas frequently exceeds the quantity required as catalyst and accordingly leads, in appropriate circumstances, to an excessive content of ammonium sulfate in the acetone cyanohydrin which has been stabilised with sulfuric acid. In such cases it is advantageous to subject the crude gas firstly to an acid washing in order to eliminate ammonia from the crude gas. In the case where an acid-washed crude gas is employed, however, a suitable basic catalyst then has to be added to the gas/liquid reactor in catalytically effective quantity. In principle, the known inorganic and organic basic compounds can be employed as catalyst, but organic amines are preferably employed. According to a particularly preferred embodiment, use is made of a tertiary amine, in particular a tertiary amine with a boiling-point of at least 60° C. Tertiary amines such as triethylamine, tri-n-propylamine, tri-n-butylamine and N-methylmorpholine are highly suitable. The quantity of catalyst required expediently lies within the range from 1 to 100, in particular 1 to 20, millimoles per mole of hydrogen cyanide employed. In these embodiments the amine-type catalyst is preferably introduced into the gas/liquid reactor together with the acetone.

The gas/liquid reactor that is employed for the formation of acetone cyanohydrin may be a reactor of arbitrary structural design, provided that an adequate contact between the gas phase and the liquid phase is guaranteed. These reactors are preferably multi-stage reactors. Examples of suitable reactors are several stirrer vessels connected in series, a combination of stirrer vessel and reaction tube, reactors with continuous circulation (air-lift principle), bubble columns and reaction columns with trays and/or packings. For the conversion according to the invention, a reaction column with at least two separation stages is particularly preferred. In the case of tray-type columns, the trays may take the form of bubble-cap trays or sieve trays or some other form. In the case of columns with packings, those packing elements are preferred which, on the one hand, enable an intense gas/liquid contact but, on the other hand, keep the loss of pressure within acceptable limits. A person skilled in the art will ascertain the optimal number of separation stages by means of tentative experiments and/or calculations, taking the phase equilibria into account.

Gas-washers known as such with one or preferably more separation stages are suitable for washing the gas phase emerging from the reactor phase. The gas-washers are preferably wash columns which may be free of built-in parts or which may contain conventional column trays or which may be filled with conventional packing elements in one column unit or in several column units.

According to a particularly preferred embodiment, both the reactor and the gas-washer take the form of a multi-stage column. In expedient manner, in one such combination the HCN-containing gas mixture is supplied in the lower part of the reaction column, and below this supply-point the reaction mixture containing acetone cyanohydrin is carried away. Acetone and, if required, a basic catalyst are fed in the upper region of the reaction column, being preferably fed into the latter in the top thereof. The crude acetone cyanohydrin which is removed at the bottom of the reaction column is freed, after stabilisation, of acetone and hydrocyanic acid by distillation with a mineral acid such as sulfuric acid. The acetone that has been recovered in this way and the unconverted hydrocyanic acid are recycled into the reaction column. The gas mixture emerging from the reactor is passed into the wash column and washed in countercurrent with stabilised pure acetone cyanohydrin. The term 'stabilised' stands for an acidic pH value of the acetone cyanohydrin; 'pure' means that acetone and hydrocyanic acid have been largely distilled off beforehand. The stabilised pure acetone cyanohydrin that is employed for the purpose of washing may also contain water.

Instead of the conventionally preferred countercurrent guidance of the gas phase and liquid phase in the reaction column and in the washer, use may also be made of reactors and gas-washers equipped with static-mixer elements, in which the liquid phase and gas phase are guided in co-current flow. With such a design the crude acetone cyanohydrin is removed at the top of the reaction column, and the acetone cyanohydrin for washing purposes, just like the gas phase emerging from the reactor, is fed into the wash column at the bottom of the wash column.

The quantity of [sic] ammonia introduced into the system with the gas mixture containing hydrogen cyanide, or a basic catalyst supplied to the system in some other way, have [sic] to be present in the reactor in such a quantity that, despite the acid (=stabiliser) that has been introduced with the acetone cyanohydrin for washing purposes, in the largest part of the reactor the catalyst is present in catalytically effective quantity—that is to say, the acid does not suffice for complete neutralisation of the basic catalyst.

The formation of acetone cyanohydrin is conventionally carried out at normal pressure or at slight overpressure or underpressure. In expedient manner the conversion is carried out at a temperature below 60° C., in particular below 40° C. According to the particularly preferred embodiment, using a reaction column and a wash column, the conversion takes place at a temperature in the range from 20 to 40° C. The gas-washer is preferably operated at a temperature below the temperature prevailing in the reactor. Accordingly the temperature in the gas-washer lies below 40° C., preferably below 30° C. and in particular in the range between approximately 5 and 25° C. In the case where use is made of a acetone cyanohydrin for washing purposes that has been cooled to approximately 5° C. (stabilised pure acetone cyanohydrin), good results of washing are achieved, so that the waste gas contains only traces of acetone and hydrogen cyanide.

Processing of the crude acetone cyanohydrin (crude ACH) which is removed from the reactor is effected in a manner familiar to a person skilled in the art. Firstly the crude ACH is stabilised by addition of an acid, then the low-boiling components HCN, acetone and water are distilled off in one or more stages. An expedient configuration for the purpose of processing the crude ACH is evident from EP 0 421 237 B1.

A significant advantage of the process according to the invention consists in the fact that acetone cyanohydrin can be obtained in simple manner, with high selectivity and with good space-time yield by using gas mixtures containing hydrogen cyanide and comprising a high proportion of inert gas. A further advantage consists in the fact that the waste gas leaving the gas-washer contains only traces of acetone, hydrogen cyanide and acetone cyanohydrin. As a result of the gas washing according to the invention, acetone is reliably washed out of the waste gas and is available again in the reactor for the formation of cyanohydrin. The combination of reactor and gas-washer allows the rates of flow to be controlled in simple manner in such a way that losses of acetone and hydrocyanic acid are substantially avoided. However, the lower the content of hydrogen cyanide in the gas mixture to be employed, the higher is the quantity of acetone cyanohydrin for washing purposes to be employed per mole of HCN in order to reduce the losses of acetone in the waste gas to a technically relevant degree—the molar ratio of acetone cyanohydrin for washing purposes to hydrogen cyanide is greater than 1 in the case where Andrussow crude gas is employed, but in the case where BMA crude gas is employed the values can be lowered to below 1 to approximately 0.5. By virtue of the process according to the invention the technical effort in order to obtain firstly liquid hydrocyanic acid from an HCN-containing crude gas becomes superfluous. At the same time the provision of a storage tank for liquid hydrocyanic acid becomes superfluous. The process according to the invention represents a positive contribution in the sense of "responsible care".

EXAMPLE

Acetone cyanohydrin was produced from acetone and crude gas, washed with sulfuric acid, arising from the BMA process. Triethylamine served as catalyst. The apparatus that was used for the conversion comprises a reaction column and a wash column, each with 10 trays. The reaction temperature in the reactor was in the range from 40 to 25° C.; the reaction temperature in the wash column was approximately in the range from 25 to 12° C. The washer was subjected to the action of stabilised pure acetone cyanohydrin with a temperature of 5° C. The compositions of the liquid phases and gas phases supplied to the system and carried away from it are evident from Table 1.

TABLE 1

Compositions and flow-rates of substances supplied and carried away

| Substance | Location[1] | HCN g/h | HCN mol/h | $N_2$ g/h | $H_2O$ g/h | Acetone g/h | Acetone mol/h | $NEt_3$ g/h (mmol/h) | ACH[2] g/h | ACH[2] mol/h |
|---|---|---|---|---|---|---|---|---|---|---|
| BMA crude gas (acid-washed) | addition R/T1 | 173.0 | 6.40 | 572.0 | 29.0 | | | | | |
| acetone and catalyst | addition R/top | | | | | 376 | 6.47 | 4.46 (44.1) | | |
| wash ACH (stabilised, pure)[3] | addition WC/T10 | | | | | | | | 276.8 | 3.25 |
| crude ACH (840.3 g/h) | removal R/bottom | 37.0 | 1.37 | | 32.8 | 69.7 | 1.20 | | 700.8 | 8.23 |
| waste gas[4] | removal WC/top | 0.294 | 0.01 | | 0.09 | 1.006 | 0.017 | | 0.21 | 0.002 |

[1]R = reactor, WC = wash column, T = tray (with tray-No.)
[2]ACH = acetone cyanohydrin
[3]ACH for washing purposes, stabilised 0.6 mmol $H_2SO_4$/mol ACH, ACH content 99 wt. %
[4]The waste gas was passed through a cold trap, condensate quantity 1.6 g/h.

Table 2 shows some analytical data pertaining to the liquid phase along the combination of reaction column and wash column.

TABLE 2

| | Compositions (figures in wt. %) | | | |
|---|---|---|---|---|
| | HCN | Acetone | ACH | $H_2O$ |
| Reaction column | | | | |
| Tray No. 2 | 4.65 | 6.3 | 84.5 | 4.6 |
| Tray No. 4 | 2.2 | 12.3 | 83.8 | 1.8 |
| Tray No. 6 | 0.3 | 43.8 | 54.9 | 1.0 |
| Tray No. 8 | 0.1 | 69.3 | 29.9 | 0.7 |
| Tray No. 10 | 0.1 | 77.6 | 21.7 | 0.6 |
| Wash column | | | | |
| Tray No. 1 | 0.2 | 59.9 | 39.6 | 0.4 |
| Tray No. 5 | 0.15 | 25.6 | 74.0 | 0.4 |
| Tray No. 8 | 0.2 | 7.0 | 92.3 | 0.5 |

What is claimed is:

1. A process for the continuous production of acetone cyanohydrin, comprising conversion of hydrogen cyanide with acetone in the presence of a basic catalyst and acetone cyanohydrin in a gas/liquid reactor to which acetone and a gas mixture containing hydrogen cyanide and inert gases are supplied continuously and from which a liquid phase containing acetone cyanohydrin and a gas phase containing the inert gases are carried away, and separation of volatile constituents from the liquid phase by distillation, characterized in that the gas phase which has been carried away out of the reactor is freed of unconverted hydrogen cyanide and acetone in a gas-washer which is subjected to the action of a solvent boiling at 100 to 200° C. at normal pressure or of acidically stabilized pure acetone cyanohydrin substantially free of acetone and hydrogen cyanide, and the washed phase which is obtained is supplied to the gas/liquid reactor.

2. Process according to claim 1, characterised in that the gas phase is washed with stabilised pure acetone cyanohydrin.

3. Process according to claim 1, characterised in that a multi-stage reaction column is used by way of gas/liquid reactor.

4. Process according to claim 1, characterised in that a multi-stage wash column is used by way of gas-washer.

5. Process according to claim 1, characterized in that the gas mixture containing hydrogen cyanide and inert gases exhibits a composition which results from the methane ammonia (BMA) process or the Andrussow process for the production of hydrogen cyanide.

6. Process according to claim 1, characterised in that the conversion is carried out in a multi-stage reaction column by the gas mixture containing hydrogen cyanide being fed into the lower part of the reaction column and by acetone being fed into the upper part and by the liquid phase containing acetone cyanohydrin being removed from the bottom of the reaction column, by said liquid phase being stabilised with an acid for the purpose of obtaining stabilised pure acetone cyanohydrin and then being freed of low-boiling components by distillation, and the gas phase emerging at the reaction column is washed in countercurrent with stabilised pure acetone cyanohydrin in a multi-stage was column.

7. Process according to claim 1, characterised in that an organic amine is additionally fed continuously into the gas/liquid reactor by way of catalyst.

8. Process according to claim 1, characterized in that an acid-washed crude gas arising from methane ammonia (BMA) process or the Andrussow process and additionally an organic amine, are fed continuously into the gas/liquid reactor by way of catalyst.

9. Process according to claim 1, characterised in that 0.3 to 3 moles of stabilised pure acetone cyanohydrin are fed into the gas-washer per mole of the hydrogen cyanide introduced into the gas/liquid reactor.

10. The process according to claim 8 wherein the organic amine is triethylamine.

* * * * *